United States Patent [19]
Haertl et al.

[11] Patent Number: 5,465,581
[45] Date of Patent: Nov. 14, 1995

[54] ANALYTICAL SYSTEM HAVING ENERGY EFFICIENT PUMP

[75] Inventors: Hans-Georg Haertl, Karlsruhe, Germany; Terry A. Berger, Newark, Del.

[73] Assignee: Hewlett-Packard, Palo Alto, Calif.

[21] Appl. No.: 111,354

[22] Filed: Aug. 24, 1993

[51] Int. Cl.[6] ............................................. F17C 7/02
[52] U.S. Cl. .................... 62/50.1; 62/3.2; 62/50.6; 417/313; 417/572
[58] Field of Search ........................ 62/50.1, 50.6, 62/3.2, 20; 417/313, 572

[56] References Cited

U.S. PATENT DOCUMENTS

| | | |
|---|---|---|
| 2,772,831 | 12/1956 | Cotter . |
| 2,957,422 | 10/1960 | Loeber et al. . |
| 3,744,935 | 7/1973 | Magni . |
| 4,153,063 | 5/1977 | Roselius et al. ................ 131/143 |
| 4,825,667 | 5/1989 | Benedict et al. . |
| 5,087,360 | 2/1992 | Wright et al. ................ 210/198.2 |
| 5,142,875 | 9/1992 | James ............................ 62/50.5 |
| 5,180,293 | 1/1993 | Hartl ............................. 417/366 |

FOREIGN PATENT DOCUMENTS

| | | |
|---|---|---|
| 0373445 | 1/1989 | European Pat. Off. . |
| 2254383 | 7/1992 | United Kingdom . |

*Primary Examiner*—Ronald C. Capossela
*Attorney, Agent, or Firm*—Mark Z. Dudley

[57] ABSTRACT

A pumping system for pumping fluids at sub-ambient temperatures where the pumping fluid, after it has been used for its analytical application, is expanded such that the energy of expansion of the pumping fluid can be employed for cooling the pump head or pumping fluid prior to pumping.

10 Claims, 5 Drawing Sheets

5,465,581

ANALYTICAL SYSTEM HAVING ENERGY EFFICIENT PUMP

FIELD OF THE INVENTION

The present invention relates to the pumping of compressible pumping fluids for use with analytical apparatus and in particular, controlling the expansion of the pumping fluid to ambient pressure such that the energy of expansion can be used to cool the pumping fluid to sub-ambient temperatures prior to pumping.

BACKGROUND OF THE INVENTION

Supercritical Fluid Chromatography (SFC) and Supercritical Fluid Extraction (SFE) apparatus typically include pumping systems for pumping highly compressible fluids (for example, liquified $CO_2$), at flow rates on the order of 5 g/min. Maintaining the pumping fluid at sub-ambient temperatures prior to pumping reduces the compressibility of a compressible pumping fluid such that it can be accurately pumped.

It is known that direct application of a cryogenic fluid may be used to cool the pump head of pumping apparatus, however, an independent source of cryogenic fluid is typically employed. U.S. Pat. No. 5,142,875 entitled "Cooled Pumping System" discloses a single source of cryogenic fluid applied to a heat exchanger through cryogenic input nozzle 112 to simultaneously cool the pump head and the pumping fluid prior to and during pumping, thus reducing the bulk modulus of the pumping fluid. Since the compression stage is now isothermal, tile solvent delivery is relatively accurate and the mass flow can be easily calculated using tile first law of thermodynamics and mass conservation equations. In particular, the pump head 110 acts as a heat exchanger in which cryogenic fluid may be supplied to a cryogenic input nozzle 112 and expanded to ambient pressure. The expanded cryogenic fluid simultaneously cools the pre-cooler supply tube 116, the pump head 110 and ultimately, the pumping fluid which is input through the pumping fluid input 118. The pump head 110 is made of a material having a much higher thermal conductivity than the rest of the pump body. A thermal insulator 120 is disposed between the pump head and the pump body such that the pump head is effectively thermally insulated from the pump body. The precooler supply tube 116 is thermally coupled to a channel 117 along the top of the pump head. Since the length of tube is relatively long in relation to the tube diameter, it acts as a heat exchanger and dissipates heat from the pumping fluid to the pump head.

The use of thermoelectric cooling elements to transfer heat from a pump head and to a heat sink is disclosed in the prior art pumping system illustrated in FIG. 2 and is fully described in U.S. Pat. No. 5,180,293 entitled "Thermoelectric Pumping System". The pumping system includes a pump head 220 which is thermally isolated from the body of the pump. Since the temperature of the pumping fluid after pumping does not affect the accuracy with which the fluid is pumped, a counterflow heat exchanger 210 is employed to utilize the relatively cool pumping fluid exiting the pump to precool the fluid entering the pump prior to pumping. A second heat exchanger 230 is coupled to the pump head 220 and thermoelectric elements 240 in very close proximity to the pump head inlet such that the thermoelectric elements 240 reduce the temperature of the pumping fluid just prior to pumping. Thermoelectric elements 240 pull heat from the pump head such that it can be dissipated by the heat sink 250. Thermoelectric elements have the ability to generate a temperature differential of approximately 70 degrees centigrade between their hot and cold sides. However, the total amount of heat they are capable of removing is inversely related to the temperature differential across them. As the ambient temperature surrounding the pumping system approaches 70 degrees centigrade above the temperature of the pumping apparatus, thermoelectric cooling becomes inefficient and accurate temperature regulation of the pumping fluid is difficult.

SUMMARY OF THE INVENTION

The pumping system of this invention decreases the temperature of the pumping fluid to the point where it becomes relatively incompressible to provide for accurate flow regulation. Since the pumping fluid is already at a very high pressure, energy is absorbed when it is expanded to ambient pressure. Typically, this energy of expansion is useful as the pumping fluid, after being used for its analytical purpose, is vented away from analytical instrument. The invention lowers tile temperature of tile pumping system and pumping fluid on analytical apparatus suitable for use in SFC or SFE application by incorporating an expansion heat exchanger for utilizing the energy of expansion of the pumping fluid for pre-cooling. Expansion cooling in combination with thermoelectric cooling can be used to accurately regulate the temperature of the pumping fluid to sub-ambient temperatures just prior to pumping. Alternatively, optimized insulation in combination with an expansion heat exchanger can pre-cool the pumping fluid where accurate temperature regulation is not required.

In particular, an analytical apparatus includes a source of liquified pumping fluid at a set pressure (typically 74 bar for $CO_2$ at room temperature) coupled to a pumping system for pumping the pumping fluid at a specified mass flow rate. The pumping system has an insulated pump head with an inlet coupled to the source of pumping fluid and an outlet coupled to either a separation column for SFC or an extraction chamber for SFE. Pumping fluid exiting the analytical apparatus is directed to a pressure regulator and an expansion heat exchanger which is thermally coupled to tubing directing the pumping fluid to the pump head. The pressure regulator regulates the amount of pumping fluid to be expanded to ambient pressure.

Thermoelectric cooling elements in combination with the expansion heat exchanger provide precise control of pump head and pumping fluid temperature. The efficiency of thermoelectric elements increases as the temperature differential between the target temperature (sub-ambient) and supply temperature is minimized. The energy of expansion of the pumping fluid is used to pre-cool the pumping fluid entering the pump to minimize the cooling requirements imposed on the thermoelectric cooling elements.

Where precise control of the pumping fluid temperature is not as important, a well insulated pump head and an expansion heat exchanger/pressure regulator provide the capacity to effectively cool the pumping fluid. An initial period of operation may be required to bring the pumping fluid down to sub-ambient temperatures prior to normal operation.

In SFE the energy of expansion derived from expanding the pumping fluid during the extraction process is utilized to cool the pump head without the need for an external source of cryogenic fluid. The pump head is mounted in thermal contact with the SFE trap such that expansion of the pumping fluid within the trap cools the trap and the thermally coupled pump head. Additionally, the trap may include an external heater to heat the extraction chamber after extraction to assist in the removal of extracted components from the trap.

BRIEF DESCRIPTION OF THE DRAWINGS

These and further features of the present invention will be better understood by reading the following detailed description of the drawings in which.

DESCRIPTION OF THE PREFERRED EMBODIMENT

Figure 1:
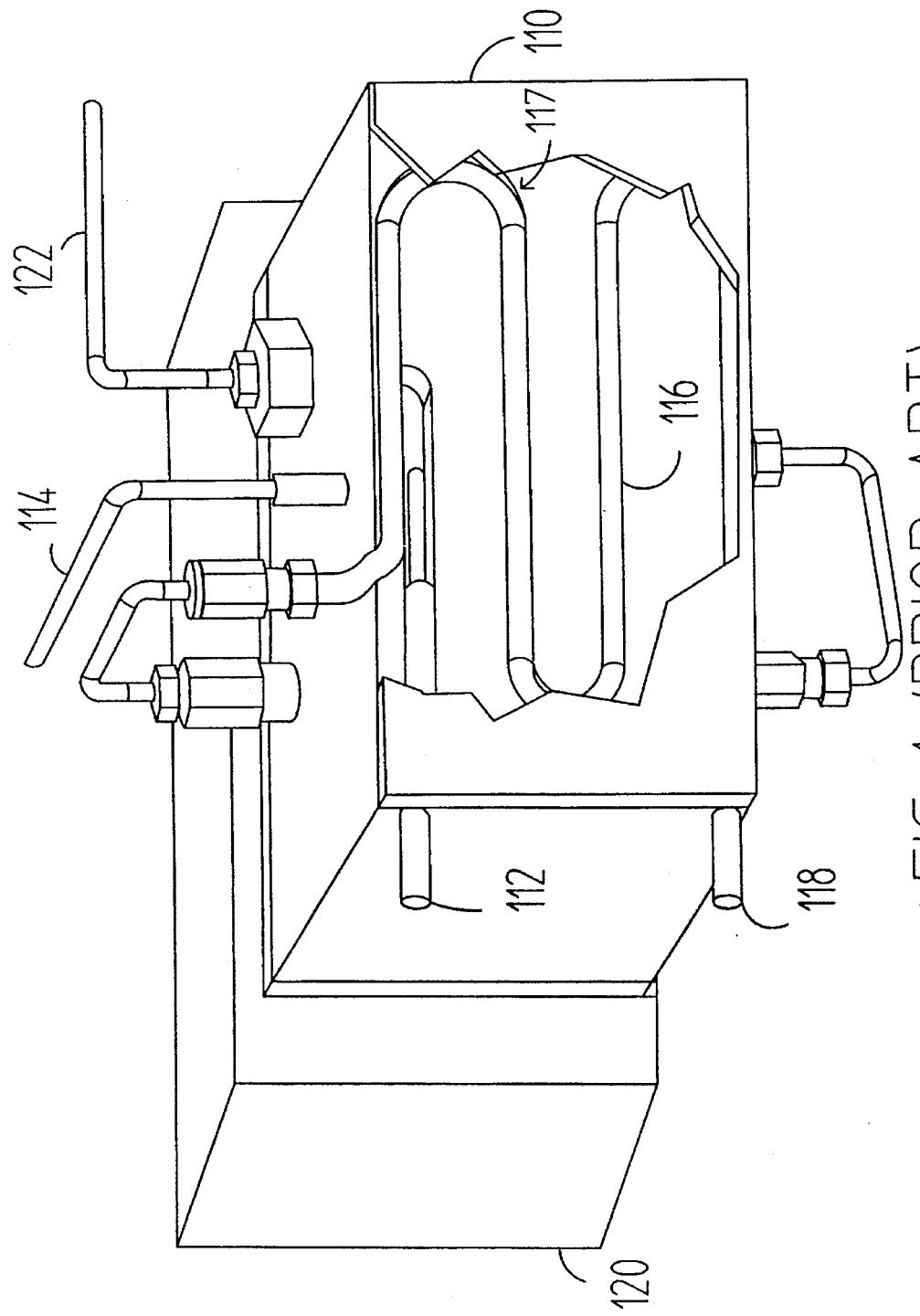
FIG. 1 is a perspective view of a prior art pumping system in which cryogenic fluid is introduced into the pump head to cool the pumping fluid to sub-ambient temperatures.
Figure 2:
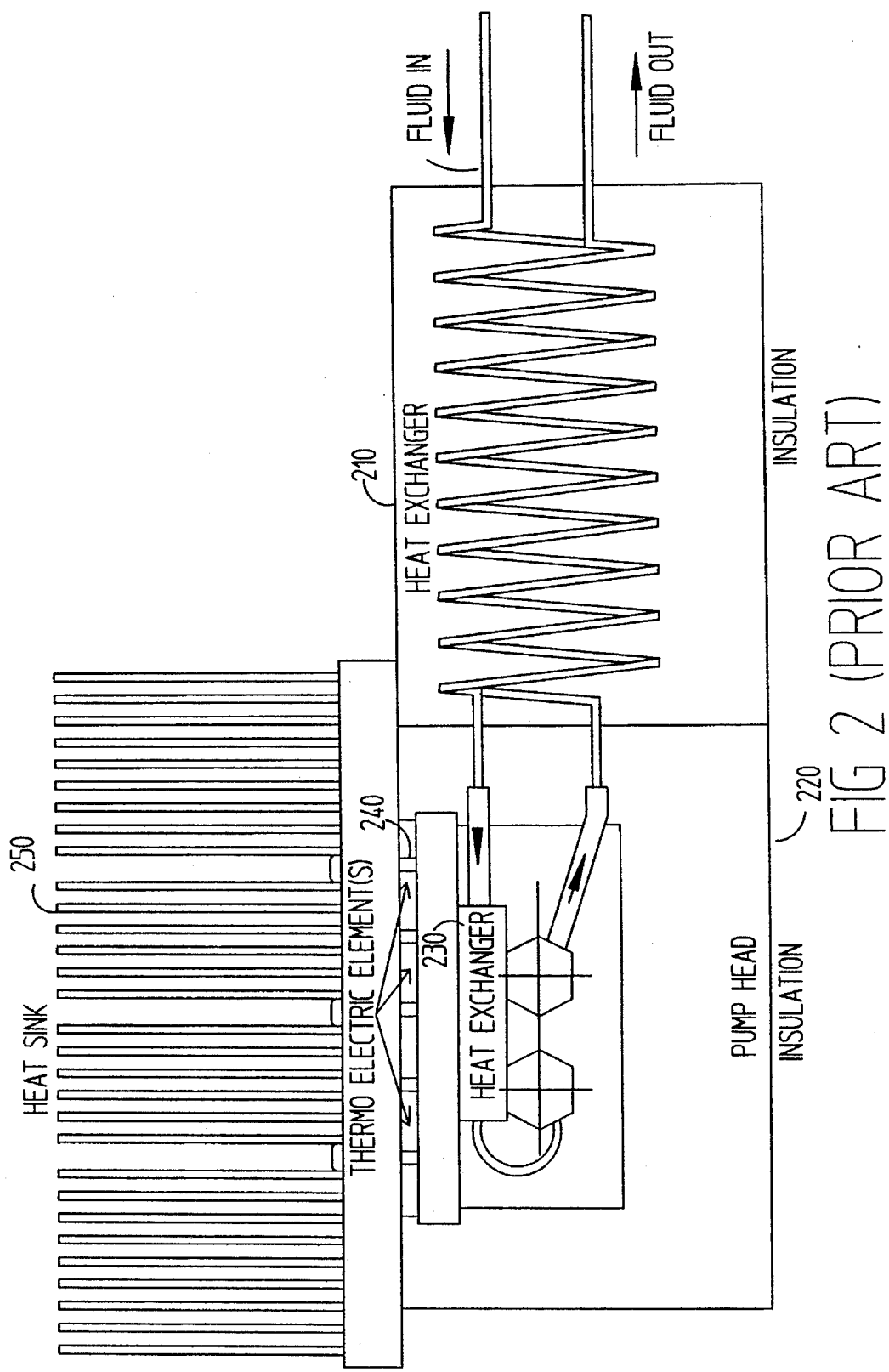
FIG. 2 is a plan view of a prior art pumping system in which thermoelectric elements a heat sink and two heat exchanger are employed for cooling the pump head and pumping fluid to sub-ambient temperatures.
Figure 3:
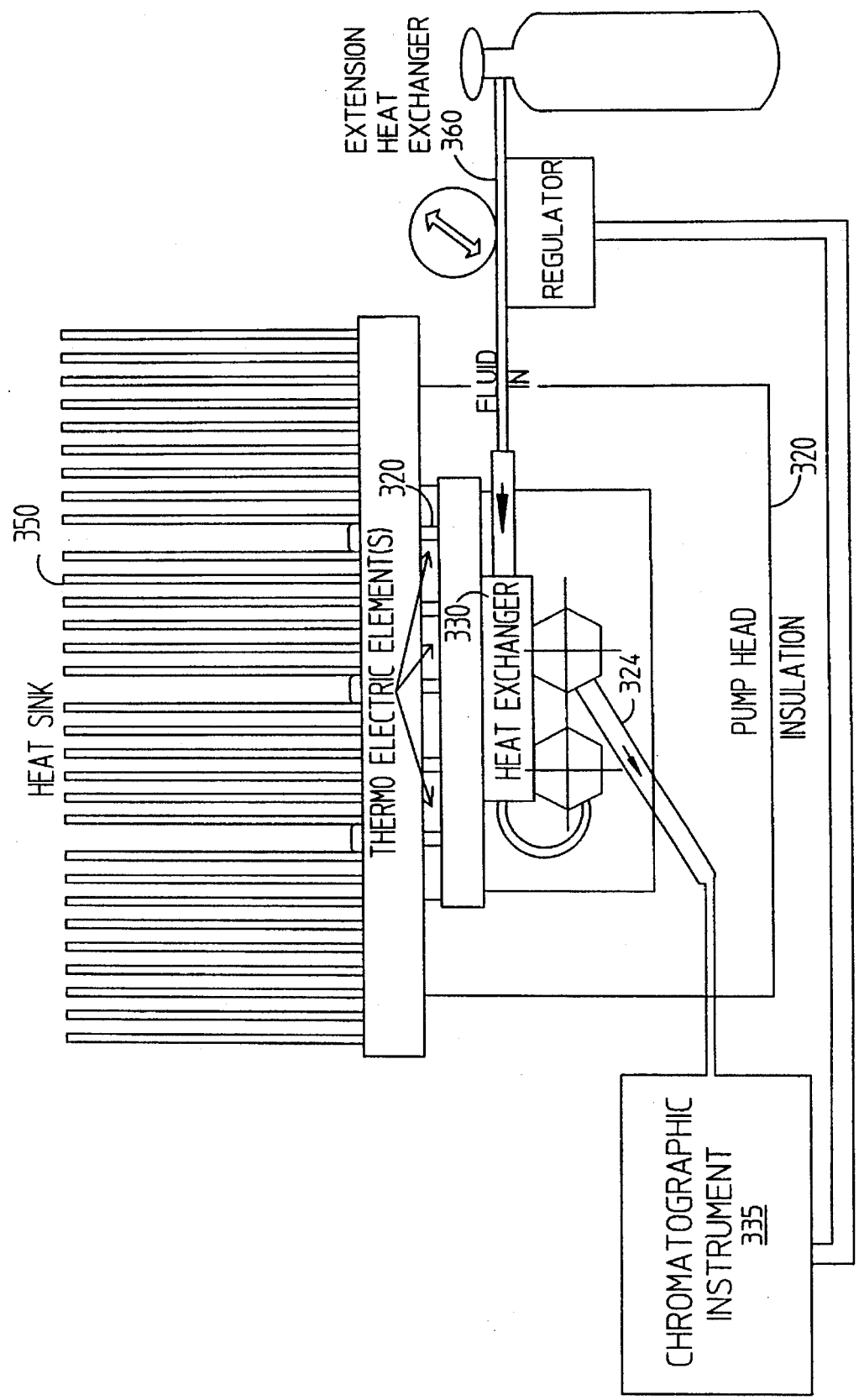
FIG. 3 is a plan view of the preferred embodiment of the invention.

FIG. 3 illustrates the preferred embodiment of the invention in which the pumping system for a SFC instrument employing thermoelectric elements 340 and a heat sink 350 coupled to a heat exchanger 330. The thermoelectric elements 340 transfer heat away from the heat exchanger 330 and to the heat sink 350. After the pumping fluid exits the analytical apparatus, it enters an expansion heat exchanger/pressure regulator 360 to provide controlled expansion of the pumping fluid to ambient pressure. Controlling the expansion of the pumping fluid provides for regulating the energy of expansion so that the pumping fluid can be cooled prior to entering the pump head. The outlet of the heat exchanger/pressure regulator 360 is in close proximity to the pump head 320 of the pump 330 such that the temperature of the pumping fluid does not increase significantly after leaving the heat exchanger. Since the bulk modulus of the pumping fluid is reduced and maintained at a desired level, there is negligible compression upon pumping. The pumping system may be incorporated into either a supercritical fluid chromatograph where the pumping fluid is used as the carrier fluid or a supercritical fluid extractor where the pumping fluid is used as a solvent to extract components from a sample.

Figure 4:
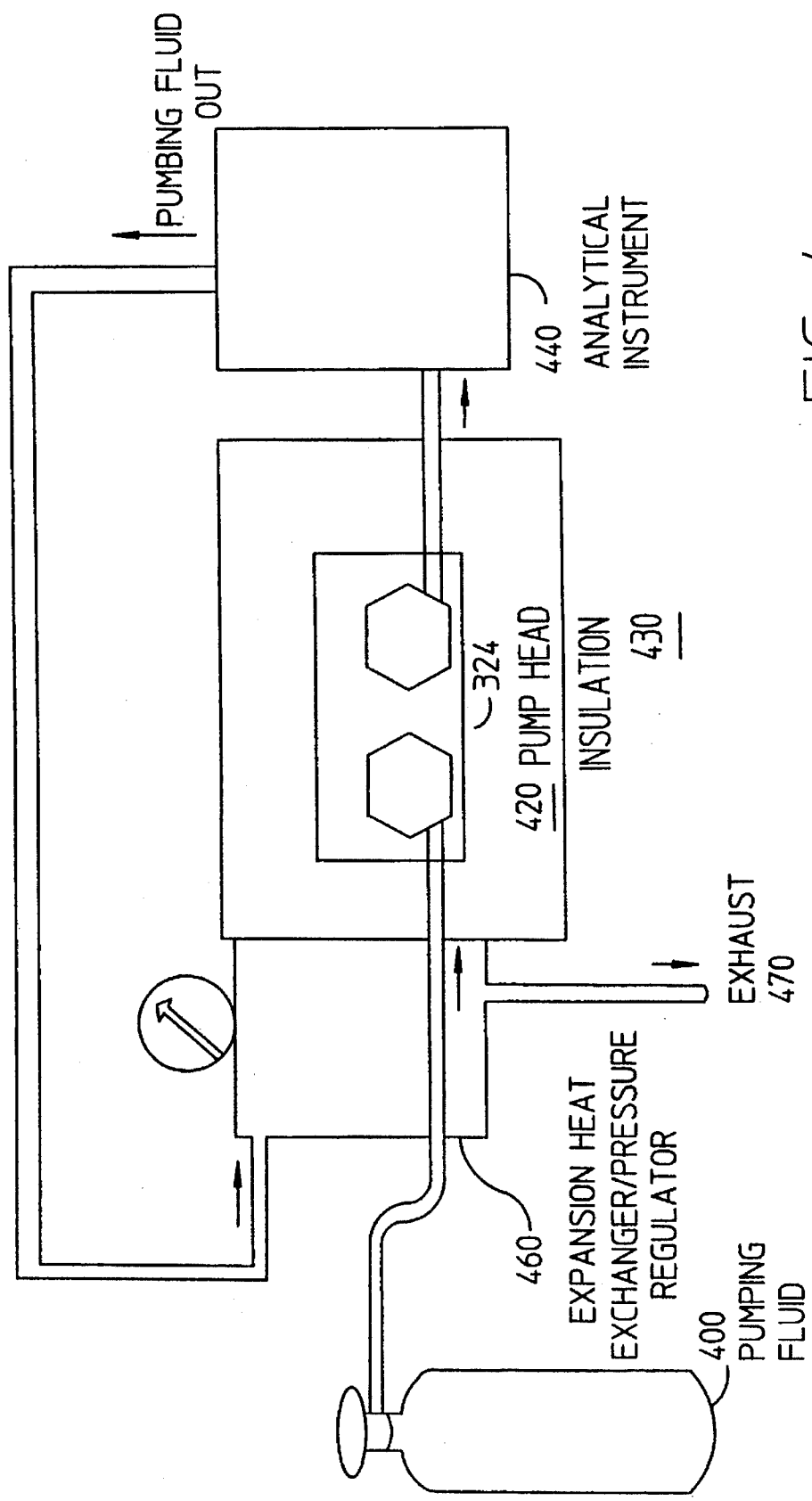
FIG. 4 is a plan view of another preferred embodiment of the invention.

FIG. 4 illustrates an alternative preferred embodiment of the invention in which pumping fluid from a source 400 is cooled prior to pumping as it passes through an expansion heat exchanger/pressure regulator 460. The pump head 420 includes insulation 430 to reduce the amount of cooling required to keep the pump head at sub-ambient temperatures. Pumping fluid exiting the pump head is directed to analytical instrument 440. The pumping fluid exits the analytical instrument 440 and is directed to expansion heat exchanger 460 where it is expanded to ambient pressure and exits at exhaust 470. The energy of expansion is employed for cooling the heat exchanger/pressure regulator 460. This embodiment is particularly suited for SFC as a continuous flow of pumping fluid is expanded during the chromatographic process.

Figure 5:
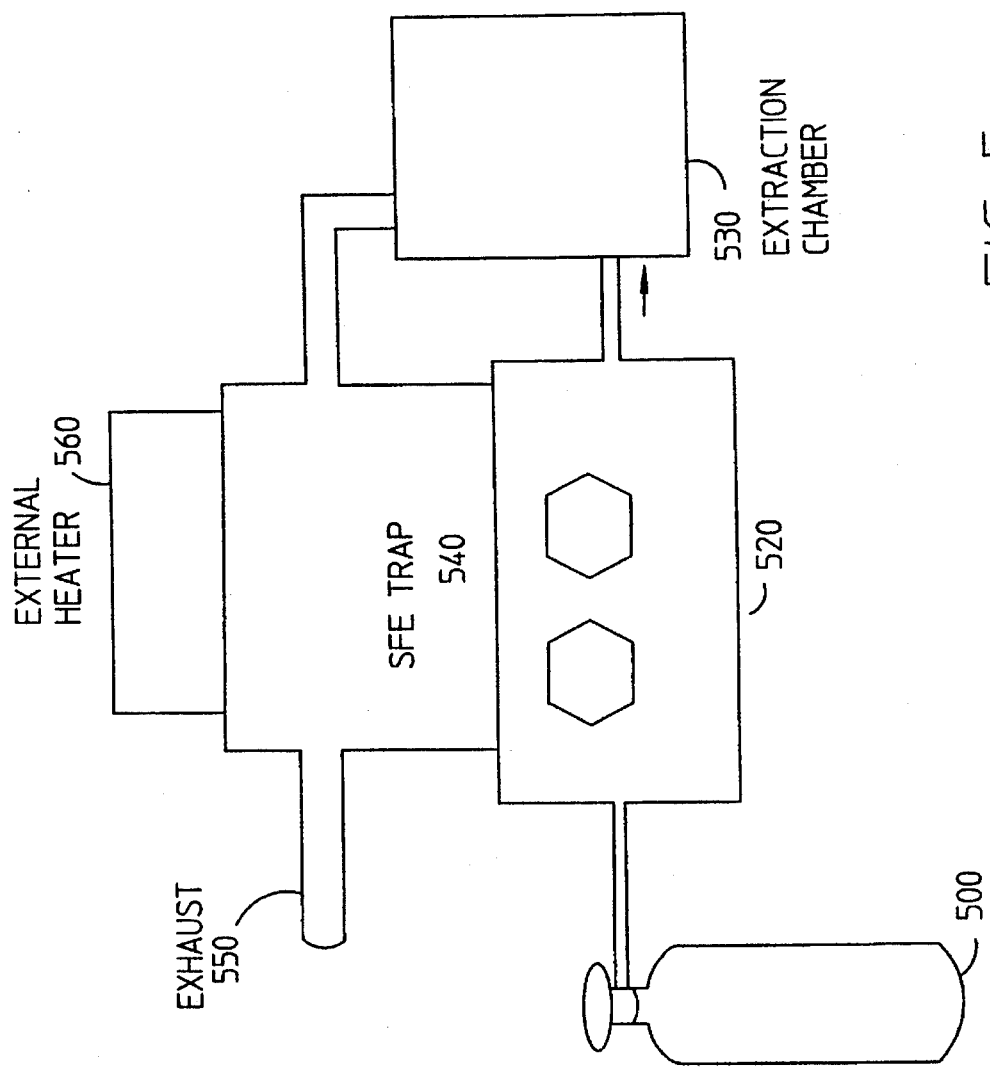
FIG. 5 is a plan view of another preferred embodiment of the invention.

FIG. 5 illustrates another embodiment of the invention employed on an SFE apparatus in which pumping fluid from a source 500 is coupled to pump head 520. SFE trap 540 is thermally coupled to the pump head 520. The pumping fluid exits the pump head and enters an extraction chamber 530 as a solvent for SFE extraction. When the extraction process is completed, the pumping fluid is directed to SFE trap 540 and expanded to ambient pressure. The energy of expansion that is absorbed upon expansion of the pumping fluid to ambient pressure is used to cool the pump head. An external heater 540 may be employed to heat the trap to assist in the removal of the extracted components.

Although best results are obtained by the foregoing pumping systems, changes and modification of the invention, as set forth in the specifically described embodiments, can be carried out without departing form the scope of the invention which is intended to be limited only by the scope of the appended claims.

I claim:

1. A pumping system for providing a pumping fluid at a sub-ambient temperature comprising:

an analytical instrument having an inlet and an outlet;

a source of a first flow of the pumping fluid;

an expansion heat exchanger operatively connected to the first flow of the pumping fluid and having an inlet coupled to said analytical instrument outlet for receiving therefrom a second flow of the pumping fluid, wherein said heat exchanger transfers heat from the first flow of the pumping fluid to the second flow of the pumping fluid; and a pump head having an inlet for receiving the first flow of pumping fluid and an outlet coupled to said analytical instrument inlet;

wherein the second flow of the pumping fluid from said analytical instrument is expanded in said expansion heat exchanger to cool the first flow of the pumping fluid to the sub-ambient temperature.

2. The pumping system of claim 1, wherein the pump head further comprises insulation to minimize the amount of cooling required to maintain the pumping fluid at the sub-ambient temperature.

3. The pumping system of claim 1, wherein said expansion heat exchanger further comprises a pressure regulator.

4. The pumping system of claim 1, comprising: a pump head heat exchanger coupled to said pump head, said pump head heat exchanger further comprising thermoelectric elements for dissipating heat from said pump head and for accurately regulating the temperature of the pumping fluid prior to pumping.

5. The pumping system as claimed in claim 4, wherein said expansion heat exchanger is thermally coupled to said pump head.

6. The pumping system of claim 1, wherein the analytical instrument further comprises a supercritical fluid extractor and the pumping fluid is used as a solvent in the supercritical fluid extractor.

7. The pumping system of claim 6, wherein the expansion heat exchanger is operable as a SFE trap.

8. The pumping system of claim 1, wherein the analytical instrument further comprises a supercritical fluid chromatograph and the pumping fluid is used as a carrier fluid in the supercritical fluid chromatograph.

9. An SFE system having a pump for providing a pumping fluid at a sub-ambient temperature comprising:

a pump head having an inlet and an outlet such that the pumping fluid flowing into the pump head through the inlet is compressed and output through said outlet; and an extraction system for effecting an extraction process to provide an extracted component, said extraction system being thermally coupled said pump head and having an inlet coupled to said pump head outlet and an outlet at ambient pressure, wherein the pumping fluid exits the pump head and is expanded in said extraction system for cooling the pump head, such that the pumping fluid is maintained at a sub-ambient temperature and wherein the pumping fluid is effective as a solvent in the extraction process.

10. The SFE system of claim 6, wherein the extraction system further comprises an extracted component trap and a heating element coupled to said trap to assist in removing the extracted component from the trap after extraction.

* * * * *

UNITED STATES PATENT AND TRADEMARK OFFICE
CERTIFICATE OF CORRECTION

PATENT NO. : 5,465,581
DATED : Nov. 14, 1995
INVENTOR(S) : Hans-Georg Haertl and Terry A. Berger It is certified that error appears in the above-indentified patent and that said Letters Patent is hereby corrected as shown below:

Column 1, line 32, should read: --the--. Column 2, line 22, "tile", each occurrence, should read:--the--.
Claim 9, Column 5, line 5, "coupled said pump head" should read: --coupled with said pump head--.
Claim 10, Column 6, line 4, "system of claim 6" should read: --system of claim 9--.

Signed and Sealed this

Sixth Day of August, 1996

*Attest:*

BRUCE LEHMAN

*Attesting Officer*   Commissioner of Patents and Trademarks